United States Patent [19]

Kagotani et al.

[11] Patent Number: 5,672,744

[45] Date of Patent: Sep. 30, 1997

[54] PROCESS FOR THE PREPARATION OF ACETIC ACID

[75] Inventors: Masahiro Kagotani; Yasuteru Kajikawa, both of Hyogo, Japan

[73] Assignee: Daicel Chemical Industries, Ltd., Osaka, Japan

[21] Appl. No.: 459,161

[22] Filed: Jun. 2, 1995

[30] Foreign Application Priority Data

Jun. 2, 1994 [JP] Japan ................................. 6-121054

[51] Int. Cl.$^6$ .................................................. C07C 51/12
[52] U.S. Cl. ............................................................ 562/519
[58] Field of Search ............................................. 562/519

[56] References Cited

U.S. PATENT DOCUMENTS 5,380,929  1/1995  Erpenbach et al. ..................... 562/519

*Primary Examiner*—C. Warren Ivy
*Assistant Examiner*—Rosalynd Williams
*Attorney, Agent, or Firm*—Flynn, Thiel, Boutell & Tanis, P.C.

[57] ABSTRACT

By employing a process for the preparation of acetic acid which comprises carbonylating methanol with carbon monoxide in a first reactor in the presence of a reaction fluid comprising a rhodium catalyst, methyl iodide, an iodide salt, methyl acetate and water, while continuously withdrawing the reaction fluid from the first reactor and introducing it into a flash zone to separate it into an evaporated part and an unevaporated part, characterized in that second reactor is provided between the first reactor and the flash zone and methanol is carbonylated with the carbon monoxide contained in the reaction fluid in a state in which it is dissolved therein in the second reactor with a residence time of 7 to 60 seconds at 150° to 220° C., the carbon monoxide contained in the reaction fluid withdrawn from the first reactor in a state in which it is dissolved therein can be converted into acetic acid in the second reactor through the same carbonylation as that occurring in the first reactor, which enables effective use and high recovery of carbon monoxide.

8 Claims, No Drawings

PROCESS FOR THE PREPARATION OF ACETIC ACID

BACKGROUND OF THE INVENTION

1. Field of the Invention

The present invention relates to a process for the preparation of acetic acid. In other words, the present invention relates to an effective use of carbon monoxide in the preparation of acetic acid using carbon monoxide as the starting material. The present invention is suitably applied to the preparation of acetic acid through the carbonylation of methanol with carbon monoxide.

2. Description of the Related Art

Acetic acid is prepared and consumed in a large amount as a basal chemical. Specially, acetic acid is used in the preparation of chemicals, chemical fibers, drugs, agricultural chemicals, polymers and so forth.

There have been known various industrial processes for the preparation of acetic acid, among which, a process for preparing acetic acid by the carbonylation of methanol with carbon monoxide is particularly effective. This process uses rhodium as the main catalyst and methyl iodide as the cocatalyst (see G.B. Patent Publication-A No. 1,233,121).

Now, description will be made on the preparation of acetic acid by the carbonylation of methanol with carbon monoxide.

According to an industrial process for the carbonylation of methanol using a rhodium complex as the catalyst and methyl iodide as the cocatalyst, the carbonylation of methanol is conducted by feeding methanol as the starting material, a rhodium catalyst, a reaction accelerator and so forth, continuously into a reactor into which carbon monoxide is continuously fed in at such a rate as to maintain the reaction pressure constant; the reaction fluid is continuously withdrawn from the reactor and introduced into a flash zone; a part of the reaction fluid is evaporated in this zone and transferred to the purification step, in which acetic acid (as a product) is taken out; the residue containing the reaction accelerator and so forth is recovered and circulated to the reactor; and on the other hand, a part of the reaction fluid unevaporated in the flash zone and containing the rhodium complex, reaction accelerator and so forth, is circulated to the reactor.

With respect to the above carbonylation process, there are several causes lowering the utilization factor of carbon monoxide (i.e., the ratio of the amount of carbon monoxide which is reacted with methanol to form acetic acid to the total amount of carbon monoxide fed into the reaction system). One of the causes is a side reaction, i.e., the reaction of carbon monoxide with the water contained in the reaction fluid, which is known as the shift reaction. This side reaction consumes carbon monoxide to give hydrogen and carbon dioxide, thereby lowering the utilization factor of carbon monoxide.

Another cause lowering the utilization factor of carbon monoxide is the loss of carbon monoxide due to purging it outside the system. Specifically, the hydrogen and carbon dioxide generated by the above shift reaction accumulate in the gas-phase area of the reactor; if these gaseous by-products are not removed from the reactor, the partial pressure of carbon monoxide will lower when the total pressure in the reactor is maintained at a constant level. This lowering in the partial pressure of carbon monoxide will bring about a lowering in the carbonylation rate to make the carbonylation difficult. Therefore, the gaseous by-products must be removed from the gas-phase area of the reactor, while carbon monoxide must be fed into the reactor at such a rate as to maintain the partial pressure of carbon monoxide above a necessary level. However, the removal of hydrogen, carbon dioxide and methane from the reactor is accompanied by that of carbon monoxide therefrom, because hydrogen, carbon dioxide and methane form a gaseous mixture together with carbon monoxide in the reactor and the separation of carbon monoxide from the other components is difficult. Accordingly, as the amount of hydrogen and carbon dioxide generated increases., i.e., as the amount of carbon monoxide to be consumed in the side reaction with water increases, the amount of carbon monoxide to be removed from the reactor together with the gaseous by-products increases to result in a lowered utilization factor of carbon monoxide.

Recently, a process which lowers the water concentration of the reaction fluid has been proposed as an improvement in the carbonylation of methanol for the purpose of reducing the above losses of carbon monoxide. Specifically, Japanese Patent Publication-B No. 4-69136 (published on Nov. 5, 1992) discloses that the water concentration of the reaction fluid can be lowered by adding an alkali metal iodide or the like as a catalyst stabilizer. According to this technique, the reaction of carbon monoxide with water, i.e., the shift reaction, can be inhibited, by which the loss of carbon monoxide due to the shift reaction is reduced. Further, the amount of hydrogen and carbon dioxide generated can be reduced and also the amount of methane generated can be reduced by virtue of this reduction in the amount of hydrogen generated, by which also the amount of carbon monoxide purged from the reaction system together with hydrogen, carbon dioxide and methane can be reduced.

There is another cause for lowering the utilization factor of carbon monoxide in the carbonylation of methanol, i.e., the presence of carbon monoxide contained in the reaction fluid withdrawn from the reactor in a state in which it is dissolved therein. This carbon monoxide is separated in the flash zone and discharged from the top thereof. Such a loss of carbon monoxide cannot be reduced by conventional means such as modification of reaction conditions or change of catalysts. The examination effected by the present inventors has revealed a serious problem of carbon monoxide loss in the flash zone caused by the dissolution thereof in the reaction fluid having a low water concentration.

In order to solve the above problem, it has been thought that the carbon monoxide discharged from the system is re-fed into the reactor. However, the carbon monoxide discharged from the flash zone is present as a mixture with hydrogen, carbon dioxide and methane, so that when the mixture is re-fed as such into the reactor, hydrogen, carbon dioxide and methane accumulate in the reactor to lower the partial pressure of carbon monoxide. Therefore, the above technique necessitates the isolation of carbon monoxide from the mixture prior to the re-feeding into the reactor.

There have been disclosed several processes for the isolation of carbon monoxide from the mixture. One of the processes is a pressure swing adsorption process, which comprises making only carbon monoxide adsorbed on a specific adsorbent to be purified. However, this process has problems in that large equipment is necessary, which results in a high plant investment and that carbon monoxide cannot be recovered completely. Another of the processes is a low-temperature fractionation process, which comprises liquefying the gaseous mixture by cooling and distilling the liquefied mixture. This process as well as the above process has problems in that large equipment is necessary and that carbon monoxide cannot be recovered completely.

As described above, the processes of separating the carbon monoxide discharged from the flash zone from the other components and re-feeding it into the reactor according to the prior art failed in the complete recovery of the carbon monoxide contained in the reaction fluid in a state in which it is dissolved therein.

DISCLOSURE OF THE INVENTION

Summary of the Invention

Under these circumstances, the present inventors have made studies on the possibility of converting the carbon monoxide contained in the reaction fluid in a state dissolved therein into acetic acid without the feeding of carbon monoxide prior to the separation of the reaction fluid in the flash zone to thereby attain the effective use of carbon monoxide. As a result of the studies, they have found that the carbon monoxide contained in the reaction fluid in a state dissolved therein can be converted into acetic acid by continuously withdrawing the reaction fluid from the reactor into which carbon monoxide is continuously fed, and making the carbon monoxide dissolved in the reaction liquid react in a second reactor without the feeding of carbon monoxide.

Further, the present inventors have also found that the addition of an inorganic iodide salt such as lithium iodide or an organic iodide salt such as a quaternary ammonium iodide is favorable to the process of the present invention comprising the above conversion of the carbon monoxide contained in the reaction fluid into acetic acid. Furthermore, they have found that the effect of the present invention is particularly remarkable when an inorganic iodide salt, such as lithium iodide, or an organic iodide salt, such as a quaternary ammonium iodide, is added and the water concentration of the reaction fluid is low. More precisely, in the carbonylation process of the prior art wherein a catalyst system not containing any iodide salt was used, the carbon monoxide contained in the reaction fluid in a state in which it is dissolved therein acted as a ligand for a rhodium complex catalyst to maintain the stability of the rhodium complex in an atmosphere containing less carbon monoxide in the steps after the withdrawal from the reactor until the return to the reactor through the flash zone, thus preventing the precipitation of the rhodium complex. Therefore, in the carbonylation process of the prior art wherein a catalyst system not containing any iodide salt was used, the reaction fluid withdrawn from the reactor had to contain a certain amount of carbon monoxide in a state in which it is dissolved therein. Accordingly, the complete consumption of carbon monoxide contained in the reaction fluid in a state in which it is dissolved therein without the feeding of carbon monoxide according to the present invention is practically unacceptable to the carbonylation process of the prior art, because the stability of a rhodium complex used as the main catalyst is deteriorates.

Meanwhile, it has been disclosed in European Patent Publication-A No. 161,874 (published on Nov. 21, 1985) and U.S. Pat. No. 5,214,203 (published on May 25, 1993) that when a catalyst system comprising a rhodium complex catalyst and an inorganic iodide salt, such as lithium iodide, or an organic iodide salt, such as a quaternary ammonium iodide is used in the carbonylation, iodide ion coordinate with the rhodium complex instead of carbon monoxide to stabilize the complex under the condition of less carbon monoxide. On the basis of this disclosure, the present inventors have presumed that when a catalyst system comprising a rhodium complex catalyst and an iodide salt is used, the stability, i.e., the solubility, of the rhodium complex may be secured, even when the carbon monoxide contained in the reaction fluid withdrawn from the reactor in a state in which it is dissolved therein is used up for the carbonylation of methanol without the feeding of carbon monoxide. The present invention has been accomplished on the basis of this presumption.

Thus, the present invention relates to a process for the preparation of acetic acid which comprises carbonylating methanol with carbon monoxide in a first reactor in the presence of a reaction fluid comprising a rhodium catalyst, methyl iodide, an iodide salt, methyl acetate and water, while continuously withdrawing the reaction fluid from the first reactor and introducing it into a flash zone to separate it into an evaporated part and an unevaporated part, characterized in that a second reactor is provided between the first reactor and the flash zone and methanol is carbonylated with the carbon monoxide contained in the reaction fluid in a state in which it is dissolved therein in the second reactor at a residence time of 7 to 60 seconds at 150° to 220° C.

In other words, the present invention relates to a process for the preparation of acetic acid which comprises reacting methanol with carbon monoxide in a reactor in the presence of a rhodium catalyst, methyl iodide, an iodide salt and water, while continuously withdrawing the reaction fluid from the reactor and introducing it into a flash zone to separate it into an evaporated part and an unevaporated part, characterized in that a post-reactor is provided between the above reactor and the flash zone and the carbon monoxide contained in the reaction fluid in a state in which it is dissolved therein is reacted with methanol in the post-reactor with at a residence time of 7 to 60 seconds and at 150° to 220° C.

As described above, the process of the present invention is not problematic in the stability of a rhodium complex, and exhibits a remarkable effect particularly in a case wherein the water concentration of the reaction fluid is low, such a case being favorable to the suppression of water gas shift reaction.

The present inventors have also found, as a result of the studies, that when the water concentration of the reaction fluid in the first reactor is lower, a larger amount of carbon monoxide is contained in the reaction fluid withdrawn from the first reactor in a state in which it is dissolved therein. In particular, the loss of carbon monoxide due to its discharge from the flash zone is remarkably high when the water concentration of the reaction fluid in the first reactor is about 4% by weight or below. The reason for this phenomenon is thought to be as follows: under the reaction condition of low water concentration, the water concentration has an influence on the carbonylation rate; more precisely, in a case wherein the water concentration of the reaction fluid is low, when the reaction fluid continuously withdrawn from the first reactor is reacted in the second reactor without the feeding of carbon monoxide, the water contained in the reaction fluid is consumed by the carbonylation to suppress the reaction consuming carbon monoxide present in a state in which it is dissolved in the reaction fluid because the methanol fed as the starting material is present in the form of methyl acetate and does not directly react with carbon monoxide and the water is necessary in the conversion of acetyl iodide to acetic acid. Accordingly, when the water concentration of the reaction fluid in the first reactor is low, it is preferable in converting the carbon monoxide contained in the reaction fluid withdrawn from the first reactor into acetic acid that the reaction time in the second reactor be lengthened or that methanol, or methyl acetate and water be added to accelerate the reaction.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The carbonylation according to the present invention is conducted in the presence of a rhodium catalyst as the main catalyst. The rhodium catalyst may take any form, as far as it can be converted into a soluble complex in the reaction fluid under the reaction conditions. Specifically, $RhI_3$, a rhodium iodide complex such as $[Rh(CO)_2I]_2$ or a rhodium carbonyl complex is effectively used. The concentration of the rhodium catalyst in the reaction fluid in the first reactor may be 200 to 1000 ppm, preferably 250 to 700 ppm.

The starting material to be used in the present invention is methanol, or a mixture comprising methyl acetate, methanol and water.

The reaction in the first reactor is conducted under a pressure of 15 to 40 kg/cm$^2$G and at a temperature of 150° to 250° C. The partial pressure of carbon monoxide has an influence not only on the amount of carbon monoxide contained therein in a state in which it is dissolved therein, but also on the usefulness of the present invention. Although a higher partial pressure of carbon monoxide gives a more remarkable effect according to the present invention, the effect according to the present invention can be attained by lengthening the time for conducting the reaction of the carbon monoxide contained in the reaction fluid withdrawn from the first reactor in a state in which it is dissolved therein or by adding a starting material such as methanol and methyl acetate to the reaction fluid withdrawn from the first reactor to thereby accelerate the reaction of the carbon monoxide, even when the partial pressure of carbon monoxide fed into the first reactor is low. Accordingly, the partial pressure of carbon monoxide may be at least that which makes it possible to conduct the carbonylation of methanol at a proper rate in the first reactor. The partial pressure of carbon monoxide in the first reactor is generally 2 to 30 atm, preferably 4 to 15 atm.

According to the present invention, methyl iodide is used as the cocatalyst. The concentration of methyl iodide in the reaction fluid in the first reactor is preferably 5 to 20% by weight. The water concentration of the reaction fluid has a great influence on the reaction. The water concentration of the reaction fluid in the first reactor may be 15% by weight or below. Although the water concentration thereof is favorably 10% by weight or below, it is preferable in this case to add an iodide salt for the purpose of stabilizing the rhodium catalyst and suppressing the side reactions.

The iodide salt may be any one generating or dissociating an iodide ion. Examples of the iodide salt include alkali metal iodides such as LiI, NaI, KI, RbI and CsI; alkaline earth metal iodides such as $BaI_2$, $MgI_2$ and $CaI_2$; and aluminum group metal iodides such as $BI_3$ and $AlI_3$. The iodide salt may be also an organic iodide salt and examples thereof include quaternary phosphonium iodides (such as an adduct of tributylphosphine with methyl iodide or hydrogen iodide and an adduct of triphenylphosphine with methyl iodide or hydrogen iodide) and quaternary ammonium iodides (such as adducts of tertiary amines with methyl iodide or hydrogen iodide, adducts of pyridines with methyl iodide or hydrogen iodide, adduces of imidazoles with methyl iodide or hydrogen iodide, and adducts of imides with methyl iodide or hydrogen iodide).

The iodide salt is used in an amount of 0.07 to 2.5 mol/l, preferably 0.25 to 1.5 mol/l in terms of iodide ion, i.e., as a molar concentration of iodide ion contained in the reaction fluid in the first reactor.

In the carbonylation according to the present invention, acetic acid is favorably used as a solvent, though any solvent inert to carbonylation may be used. Examples of the solvent include aliphatic carboxylic acids, ketones, ethers, aromatic compounds, amides and phosphate esters.

The concentration of methyl acetate in the reaction fluid in the first reactor also has an influence on the reaction rate, particularly under the condition of a low water concentration. Methyl acetate is formed by the reaction of methanol fed as the starting material with acetic acid under the reaction conditions. Accordingly, a higher methyl acetate concentration is better. However, methyl acetate must be separated in the subsequent purification step and circulated to the first reactor and much energy is necessitated for the separation and circulation thereof. In view of this, it is preferable that the concentration of methyl acetate in the reaction fluid be maintained at about 0.5 to 30% by weight.

The reaction fluid withdrawn from the first reactor in which the carbonylation is conducted is reacted in the second reactor at 150° to 220° C., preferably 180° to 200° C., for 7 to 60 seconds, preferably 7 to 30 seconds, to thereby completely consume the carbon monoxide contained in the reaction fluid in a state in which it is dissolved therein. When the reaction in the second reactor proceeds difficulty due to the low water concentration of the reaction fluid, when the acceleration of the reaction is required, or when the amount of methyl acetate contained in the reaction fluid is not enough to consume the whole carbon monoxide contained in the reaction fluid, methanol and/or methyl acetate may be added to the reaction fluid. By employing such means, the carbon monoxide contained in the reaction fluid in a state in which it is dissolved therein can be converted into acetic acid through the same carbonylation as that occurring in the first reactor, which enables the effective use and high recovery of carbon monoxide.

Now, the equipment to be used in carrying out the present invention will be described.

The process of the present invention can be carried out through the use of equipment comprising a conventional reactor (i.e., first reactor) for liquid-phase continuous carbonylation, a conventional flash zone therefor and a post-reactor (i.e., second reactor) provided between the above reactor and the flash zone. The post-reactor may have any shape, as long as the reaction fluid can be maintained at a temperature suitable for carbonylation and enough reaction time can be secured. Specifically, the post-reactor may be either a tubular reactor or a tank reactor.

EXAMPLES

The present invention will now be described in more detail with reference to the following Examples which should not be considered to limit the scope of the present invention.

Example 1

200 g of acetic acid, 20 g of water, 3.6 g of rhodium iodide and 70 g of lithium iodide were put in an autoclave having a capacity of 600 ml. Carbon monoxide (30 atom) and hydrogen (10 atm) were charged into the autoclave and the fluid in the reactor was maintained at 185° C. After two hours, the feeding of a gaseous mixture comprising carbon monoxide as the main component and 1% of hydrogen to the autoclave at a rate of 50 NL (normal liter)/hr was started. The total pressure of the autoclave was maintained at 28 $kg/cm^2G$ by operating a pressure-regulating valve. Further, methyl iodide, methanol, acetic acid and water were introduced into the autoclave at rates of 360 g/hr, 60 g/hr, 370 g/hr and 50 g/hr, respectively. The reaction fluid was withdrawn from the autoclave through a level controlling valve at a rate of 3.1 l/hr. The reaction fluid comprised 13.5% by weight of methyl iodide, 2.5% by weight of methyl acetate, 8.4% by weight of water, 71.0% by weight of acetic acid, 500 ppm of rhodium and 4.5% by weight of lithium iodide.

Then, the reaction fluid withdrawn from the autoclave was passed through a tubular reactor maintained at 190° C. with a residence time of 10 seconds. The effluent from the tubular reactor was introduced into an evaporator maintained at 1.4 $kg/cm^2G$. The vapor discharged from the evaporator was passed through a condenser to be separated into a liquid part and a gaseous part. The unevaporated part remaining in the evaporator as a liquid was returned to the autoclave with a high-pressure pump. The gaseous part was collected for one hour and the volume of the part collected was determined. Further, the gaseous part thus collected was analyzed by gas chromatography to determine the content of carbon monoxide. As shown in Table 1, no carbon monoxide was detected.

Comparative Example 1

The same procedure as that of Example 1 was repeated except that the residence time in the tubular reactor was 5 seconds. As shown in Table 1, the content of carbon monoxide in the gaseous part was 0.2 NL (normal liter).

Comparative Example 2

The same procedure as that of Example 1 was repeated except that the tubular reactor was maintained at 100° C. (not 190° C.). As shown in Table 1, the content of carbon monoxide in the gaseous part was 0.3 NL (normal liter).

TABLE 1

|  | Ex. 1 | Comp. Ex. 1 | Comp. Ex. 2 |
| --- | --- | --- | --- |
| Temp. of tubular reactor (°C.) | 190 | 190 | 100 |
| Residence time (sec) | 10 | 5 | 10 |
| Amt. of CO (NL) | 0 | 0.2 | 0.3 |

The invention being thus described, it will be obvious that it may be varied in many ways. Such variations are not to be regarded as a departure from the spirit and scope of the invention, and all such modifications as would be obvious to one skilled in the art are intended to be included within the scope of the following claims.

What we claim is:

1. A process for the preparation of acetic acid comprising the steps of:

carbonylating methanol with carbon monoxide in a first reactor in the presence of a reaction fluid comprising a rhodium catalyst, methyl iodide, an iodide salt, methyl acetate and water;

withdrawing a reaction fluid having carbon monoxide dissolved therein from the first reactor and introducing it into a second reactor;

carbonylating methanol in the second reactor with the carbon monoxide dissolved in the reaction fluid at a residence time of from 7 to 30 seconds and a temperature of from 150° to 220° C. and forming a crude acetic acid mixture; and introducing the crude acetic acid mixture into a flash zone to separate it into a vapor phase and a liquid phase.

2. The process for the preparation of acetic acid as claimed in claim 1, wherein the iodide salt is lithium iodide.

3. The process for the preparation of acetic acid as claimed in claim 1, wherein the reaction fluid in the first reactor contains the water in a concentration of up to 10% by weight.

4. The process for the preparation of acetic acid as claimed in claim 2, wherein the reaction fluid in the first reactor contains the water in a concentration of up to 10% by weight.

5. The process for the preparation of acetic acid as claimed in claim 1, wherein the residence time is from 7 to 10 seconds.

6. The process for the preparation of acetic acid as claimed in claim 1, wherein water is present in the first reaction fluid in an amount up to 15% by weight.

7. The process for the preparation of acetic acid as claimed in claim 1, wherein water is present in the first reaction fluid in an amount of from 10 to 15% by weight.

8. The process for the preparation of acetic acid as claimed in claim 1, wherein the carbon monoxide dissolved in the reaction fluid is the sole source of carbon monoxide for carbonylating methanol in the second reactor.

* * * * *